US012685688B2

(12) United States Patent
Huynh et al.

(10) Patent No.: US 12,685,688 B2
(45) Date of Patent: Jul. 21, 2026

(54) METHOD FOR MOVING AN EXOSKELETON

(71) Applicant: WANDERCRAFT, Paris (FR)

(72) Inventors: Vaiyee Huynh, Arcueil (FR); Antonio El Khoury, San Francisco, CA (US)

(73) Assignee: WANDERCRAFT, Paris (FR)

( * ) Notice: Subject to any disclaimer, the term of this patent is extended or adjusted under 35 U.S.C. 154(b) by 226 days.

(21) Appl. No.: 18/694,561

(22) PCT Filed: Oct. 6, 2022

(86) PCT No.: PCT/FR2022/051894
§ 371 (c)(1),
(2) Date: Mar. 22, 2024

(87) PCT Pub. No.: WO2023/057727
PCT Pub. Date: Apr. 13, 2023

(65) Prior Publication Data
US 2024/0390212 A1     Nov. 28, 2024

(30) Foreign Application Priority Data

Oct. 6, 2021    (FR) ........................................ 2110555

(51) Int. Cl.
*A61H 3/00*        (2006.01)
*G16H 40/63*      (2018.01)

(52) U.S. Cl.
CPC .............. *A61H 3/00* (2013.01); *G16H 40/63* (2018.01); *A61H 2201/5007* (2013.01); *A61H 2230/625* (2013.01)

(58) Field of Classification Search
CPC .. A61H 3/00; A61H 1/0237; A61H 2003/007; A61H 2201/5007; A61H 2230/625; B25J 9/0006
See application file for complete search history.

(56) References Cited

U.S. PATENT DOCUMENTS

2020/0281803 A1*   9/2020   Teng .................... A61H 1/0262

FOREIGN PATENT DOCUMENTS

WO        2015140353 A2      9/2015
WO        2015140353 A3      1/2016

OTHER PUBLICATIONS

L. Penco, E. M. Hoffman, V. Modugno, W. Gomes, J.-B. Mouret and S. Ivaldi, "Learning Robust Task Priorities and Gains for Control of Redundant Robots," in IEEE Robotics and Automation Letters, vol. 5, No. 2, pp. 2626-2633, Apr. 2020, doi: 10.1109/LRA.2020. 2972847. keywords: (Year: 2020).*

(Continued)

*Primary Examiner* — Margaret M Luarca
*Assistant Examiner* — Sarah B Lederer
(74) *Attorney, Agent, or Firm* — Thomas | Horstemeyer, LLP

(57)                ABSTRACT

The invention relates to a method for moving a bipedal exoskeleton (1) accommodating a human operator, the method being characterised in that it involves the implementation, by data processing means (11) of the exoskeleton (1), of the following steps: (a) obtaining at least one postural instruction to be applied by the exoskeleton (1) in order for the operator to perform an exercise movement; (b) determining a trajectory of the exoskeleton (1) by means of hierarchised inverse kinematics based on the at least one determined postural instruction, said hierarchised inverse kinematics comprising a stack of hierarchised tasks comprising, as the task of highest priority, a task of keeping the feet of the exoskeleton (1) on the ground as the operator performs the exercise movement.

20 Claims, 4 Drawing Sheets

(56)                    References Cited

OTHER PUBLICATIONS

Penco, et al., "Learning Robust Task Priorities and Gains for Control fo Redundant Robots", IEEE Robotics and Automation Letters, vol. 5, No. 2, Apr. 2020, pp. 2626-2633.
Escande, et al., "Fast Resolution of Hierarchized Inverse Kinematics with Inequality Constraints", 2010 IEEE International Conference on Robotics and Automation, Anchorage Convention District, May 3-8, 2010, pp. 3733-3738.
Vigne, et al., "State Estimation for a Legged Robot with multiple Flexibilities Using IMUS: A Kinematic Approach", IEEE Robotics and Automation Letters, vol. 5, No. 1, Jan. 2020, pp. 195-202.
Benallegue, et al., "Estimation and Stabilization of Humanoid Flexibility DeformationUsing Only Inertial Measurement Units and Contact Information", International Journal of Humanoid Robotics, vol. 12, No. 3 (2015), 20 pages.
Stephane Caron, et al., "Stair Climbing Stabilization of the HRP-4 Humanoid Robot Using Whole-body Admittance Control", arXiv:1809.07073v6 [cs.RO] Mar. 20, 2020.

* cited by examiner (a) Obtaining postural instruction (b) Determining a trajectory by means of hierarchized inverse kinematics with highest priority task of keeping the feet of the exoskeleton on the ground (c) Executing the trajectory

FIG. 3a

METHOD FOR MOVING AN EXOSKELETON

CROSS REFERENCE TO RELATED APPLICATIONS

This application is the 35 U.S.C. § 371 national stage application of PCT Application No. PCT/FR2022/051894, filed Oct. 6, 2022, which application claims the benefit of French Application No. FR 2110555 filed Oct. 6, 2021, both of which are hereby incorporated by reference herein in their entireties.

GENERAL TECHNICAL FIELD

The present invention relates to the field of exoskeleton type robots.

More precisely, it relates to a method for moving an exoskeleton, in a mode called exercise mode.

STATE OF THE ART

Recently, assisted walking devices called exoskeletons have appeared for people with significant mobility problems such as paraplegics, which are external robotic devices that the operator (the human user) "puts on" using a system of attachments which links the movements of the exoskeleton to his own movements. Lower limb exoskeletons have multiple joints, usually at least at the knees and hips, to replicate the walking movement. Actuators allow these joints to move, which in turn make the operator move. An interface system allows the operator to give orders to the exoskeleton, and a command system transforms these orders into commands for the actuators. Sensors generally complete the device.

These exoskeletons are a step forward from wheelchairs because they allow operators to stand up and walk. Exoskeletons are no longer limited by wheels and can theoretically evolve in the majority of urban environments: wheels, unlike legs, do not allow to overcome significant obstacles such as steps, stairs, obstacles of too great a height, etc.

In addition to recovering mobility, exoskeletons have a strong interest in rehabilitation, particularly following neurological accidents such as strokes.

"Verticalization" is in particular an important exercise in the rehabilitation of people with reduced mobility. It has a significant impact on the person, whether psychological or physical. This exercise allows them, on the one hand, to put themselves on a level with the people around them to interact socially, which is very good for their morale (self-confidence and dignity). On the other hand, it helps improve breathing, blood circulation and even digestion, and prevents muscle retraction and the appearance of bedsores.

"Exercise" mode is a mode of operation of an exoskeleton in which the patient does not move, and his two feet always remain in contact with the ground (they are immobile), in order to perform exercise movements of interest for patient rehabilitation and/or for energizing the body.

The problem is that a paraplegic cannot make a movement that will be "followed" by the exoskeleton. In the case of walking, the exoskeleton can apply a predefined trajectory, but this is no longer possible in exercise mode, because then the movement must be completely controlled by the patient, based on sensor data.

Only one exoskeleton that allows a paraplegic to perform exercises in a standing posture is known, it is the REX from RexBionics. However, it works according to a simplistic principle: the exoskeleton freezes in a given posture, and then the patient can mobilize the upper body, but without any possibility of controlling the exoskeleton.

It is understood that this solution strongly limits the possible exercise movements: REX "Rexercises" mode only allows the handling of balls and weight training equipment in the upper part of the body, whereas it would be profitable to allow the patient to perform squats, bend over to grab an object, move his hips, etc.

In addition, keeping the patient in a static posture poses some problems:

Sensation of being stuck in the exoskeleton;

Risk of the robot tipping over with the patient's large movements and consequently injuring him;

Failure to reach objects located at low altitude.

On the contrary, boosting verticalization and increasing the reaching space helps motivate the patient in this exercise and gives them control of their movements.

It would be desirable to have a new solution for moving an exoskeleton, which allows a greater variety of exercises while remaining stable and secure for the patient.

PRESENTATION OF THE INVENTION

The present invention thus relates according to a first aspect to a method for moving a bipedal exoskeleton accommodating a human operator, the method being characterized in that it includes the implementation, by data processing means of the exoskeleton, of steps of:

(a) obtaining at least one postural instruction to be applied by the exoskeleton in order for the operator to perform an exercise movement;

(b) determining a trajectory of the exoskeleton by means of hierarchized inverse kinematics based on the at least one determined postural instruction, said hierarchized inverse kinematics comprising a stack of hierarchized tasks comprising, as the task of highest priority, a task of keeping the feet of the exoskeleton on the ground during said exercise movement of the operator.

According to advantageous and non-limiting features:

The stack of hierarchized tasks further comprises at least one task of controlling the rest of the exoskeleton, of lower priority than said task of keeping the feet of the exoskeleton on the ground.

Said at least one task of controlling the rest of the exoskeleton is selected from:

a task of controlling the center of mass, CoM, of the exoskeleton;

a task of controlling the pelvis of the exoskeleton;

a task of controlling the posture of the exoskeleton.

The stack of hierarchized tasks comprises, in decreasing order of priority, said task of keeping the feet of the exoskeleton on the ground, the task of controlling the CoM of the exoskeleton, the task of controlling the pelvis of the exoskeleton, and the task of controlling the posture of the exoskeleton.

The task of controlling the CoM of the exoskeleton is a task of CoM position control and stabilization via a controller based on a flexible inverted pendulum model.

Step (b) comprises the execution of control loops defining for each task the evolution of a position of the exoskeleton so as to implement said determined trajectory.

There is an independent control loop per task, the hierarchized inverse kinematics being implemented within said control loops.

The position of the exoskeleton is defined by a vector of the joint positions of the actuated degrees of freedom of the exoskeleton.

Step (a) comprises the identification of a movement intention by the operator, from data acquired by sensors of the exoskeleton; and determining the at least one postural instruction from said movement intention.

The at least one postural instruction is a center of mass, CoM, and/or joint instruction defining a desired pose of the exoskeleton during said exercise movement of the operator.

According to a second aspect, the invention relates to an exoskeleton comprising data processing means configured to implement a method according to the first aspect for moving the exoskeleton.

According to a third and a fourth aspect, the invention relates to a computer program product comprising code instructions for executing a method according to the first aspect for moving an exoskeleton; and storage means readable by a computer equipment on which a computer program product comprises code instructions for executing a method according to the first aspect for moving an exoskeleton.

PRESENTATION OF THE FIGURES

Other features and advantages of the present invention will appear upon reading the following description of a preferred embodiment. This description will be given with reference to the appended drawings in which.

Figure 3A:
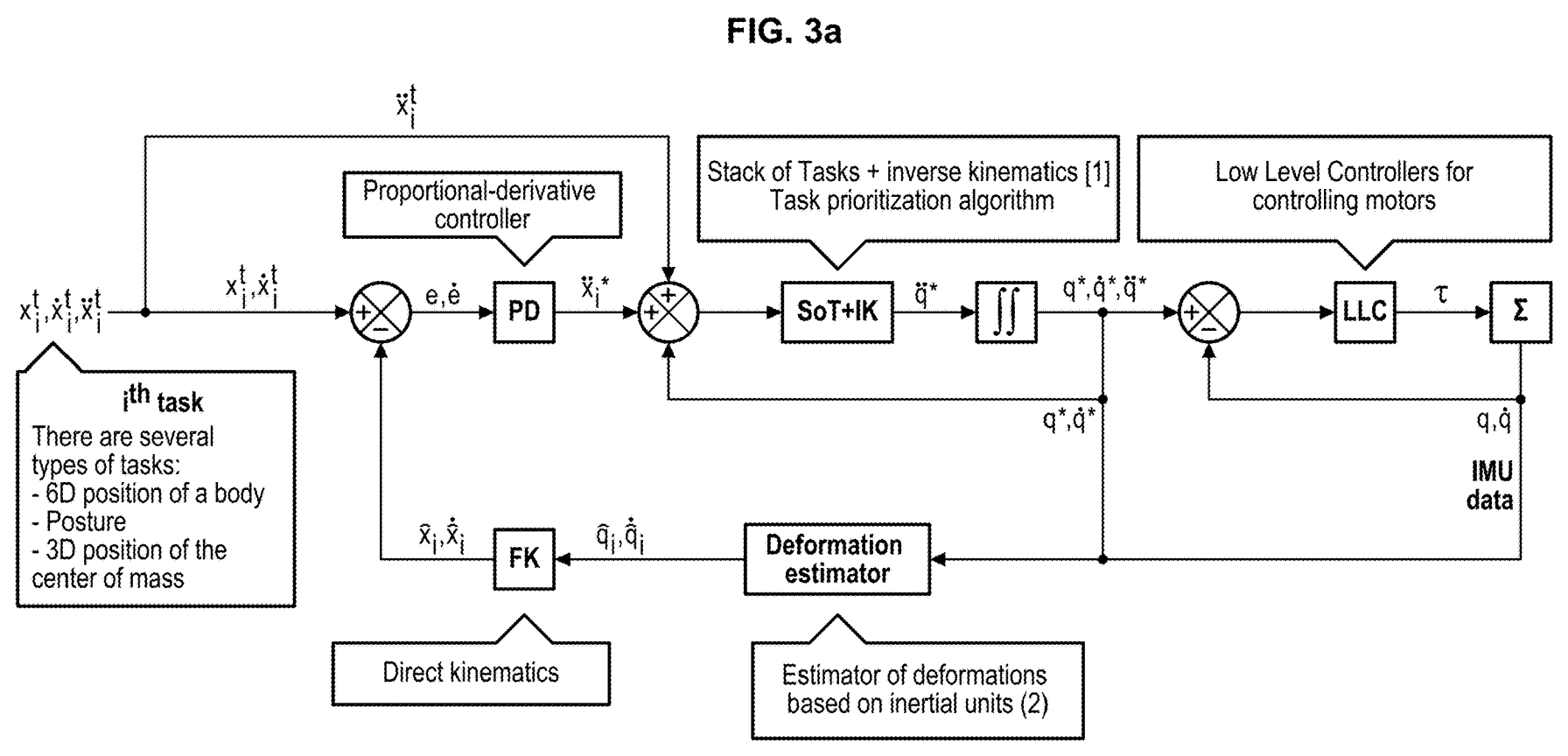
Figure 3B:
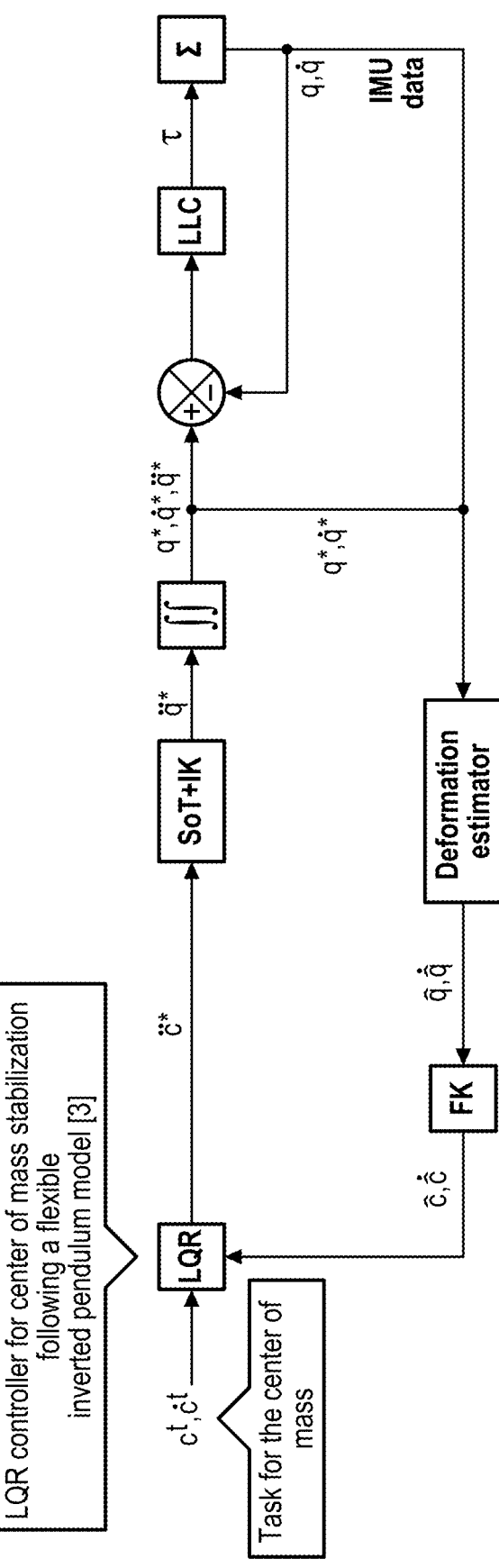

FIG. 3*a* schematically shows a first control loop used in a preferred embodiment of the method according to the invention;

FIG. 3*b* schematically shows a second control loop used in a preferred embodiment of the method according to the invention.

DETAILED DESCRIPTION

Architecture

The present invention proposes a method for moving an exoskeleton 1.

Figure 1:
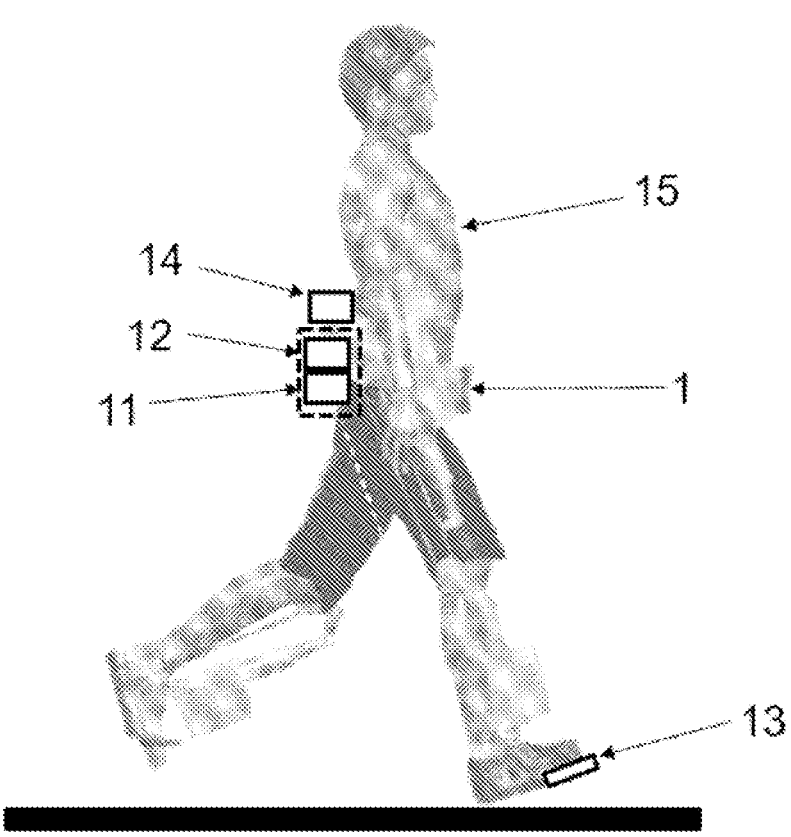
FIG. 1 is a diagram of an exoskeleton used by the methods according to the invention.

With reference to FIG. 1, said exoskeleton 1 is an articulated mechanical system of the bipedal robotic device type, which is actuated and commanded, provided with two legs, more precisely accommodating a human operator having his lower limbs each integral with one leg of the exoskeleton 1 (in particular using straps). It can thus be a more or less humanoid robot.

Here a difference will be made between the movement of the operator (which is a global movement which most often involves movements of the arms and the upper part of the body that the exoskeleton undergoes, and which will be called "exercise movement" in the context of the present invention) and the movement of the exoskeleton 1 alone or "trajectory" (which is therefore limited to the legs). In practice it is the operator who performs the 30 exercise and therefore physically moves the upper body, and the exoskeleton 1 responds by implementing a trajectory during which the feet of the exoskeleton 1 remain immobile, in contact with the ground.

In other words, in the present exercise mode, the exoskeleton 1 is moved by keeping the feet of the exoskeleton 1 fixed. It is understood that this is a constraint imposed by the exercise mode (that is to say keeping the feet on the ground is imposed by the exoskeleton 1 when it is in said exercise mode).

It is understood that the movement "during which the feet of the exoskeleton 1 remain in contact with the ground" means as opposed to a "walking" type movement which translates in practice into alternative support on the legs, in a standing position, so as to produce a movement. Typically a walking movement of the exoskeleton is composed of a sequence of steps, each step seeing a foot come off the ground then rest, before role reversal (that is to say an alternation of steps of the left foot and the right foot).

Thus, in the context of the present method there is no movement of the exoskeleton 1 due to the immobility of the feet, but the exoskeleton 1 remains in movement (and all its degrees of freedom are mobile), contrary to which was the case for example for REX, and assists the operator. The general objective of the exercise mode is to increase the patient's reaching space while stabilizing them upright when they move their upper body. It is understood in fact that it is, for example, essential that the knees of the exoskeleton 1 bend so that the user can pick up something placed on the ground in front of him.

This exercise movement carried out by the operator could for example be lift/pull/catch/throw an object with one or both arms;

bend over, possibly to pick something up;

perform rotational movements of the pelvis on one or more axes, the "rolling" movement of the pelvis (longitudinal axis rotation) being commonly called "swaying";

do squats;

do stretching;

play a sport (racket sport, boxing, basketball, etc.);

etc.

However, it will be understood that any exercise movement during which the feet of the exoskeleton 1 remain fixed can be performed without limitation within the framework of the present invention, as long as there is a way to accomplish this movement in a stable manner.

The exoskeleton 1 has a plurality of degrees of freedom, that is to say deformable joints (generally via rotation) that is to say movable relative to each other which are each "actuated", or "non-actuated". An actuated degree of freedom designates a joint provided with an actuator commanded by data processing means 11, that is to say that this degree of freedom is controlled and can be acted upon. As will be seen, some of these degrees of freedom can be "flexible".

The data processing means 11 designate computer equipment (typically a processor, either external if the exoskeleton 1 is "remote-controlled" but preferably embedded in the exoskeleton 1, see below) adapted to process instructions and generate commands to the different actuators. The latter can be electric, hydraulic, etc.

The exoskeleton 1 may further comprise data storage means 12, inertial measurement means 14 (inertia unit), means for detecting the impact of the feet on the ground 13 and, if necessary, estimating the contact forces (contact sensors or possibly pressure sensors), and/or a vest equipped with sensors 15.

The present application will not be limited to any exoskeleton architecture 1, and the example will be taken as described in applications WO2015140352 and WO2015140353.

Thus, preferably and in accordance with these requests, the exoskeleton 1 comprises on each leg a foot structure comprising a support plane on which a foot of a leg of the person wearing the exoskeleton can bear.

"The foot of the exoskeleton 1 remaining in contact with the ground", means that this structure is referred to as foot.

The person skilled in the art will, however, be able to adapt the present method to any other mechanical architecture, and it is sufficient for the exoskeleton to have two legs, each ending with a foot.

Principle

"Trajectory" of the exoskeleton conventionally means the evolutions of each degree of freedom (in particular actuated, but the non-actuated degrees can be involved in the command algorithms of the other degrees of freedom) expressed as a function of time or a phase variable. In the remainder of this description, "position" of the exoskeleton 1 will be understood as the joint positions of the actuated degrees of freedom, which are advantageously six in number per leg, that is to say a position defined by a vector of dimension 12.

It is understood that the trajectory here has the constraint of having fixed feet, but all the degrees of freedom continue to evolve.

To respect this constraint, the invention proposes to determine the trajectory by implementing "hierarchized" inverse kinematics, that is to say having a plurality of hierarchized tasks.

Inverse kinematics (often abbreviated IK) designates a solution for calculating the "position" of the exoskeleton 1 (that is to say a configuration of all its joint positions as explained) in order to obtain a desired pose. The term inverse kinematics refers to the fact that the resolution of the calculations is generally based on the kinematic equations of the joint model.

A "task" is called an inverse kinematics objective defining all or part of the desired pose (the desired pose can thus be defined as a plurality of decoupled tasks), and it is known how to obtain a control law by "stacking" a certain number of tasks hierarchized from highest priority to lowest priority. This is called in the literature SoT for "Stack of Tasks".

The resolution of inverse kinematics is generally complex from a computational point of view, especially if it comprises a plurality of hierarchized tasks, even if efficient hierarchized inverse kinematics algorithms are currently known, see for example the document *A Dedicated Quadradic Program for Fast Hierarchical-Inverse-Kinematic Resolution. A. Escande, N. Mansard and P-B. Wieber. In IEEE Int. Conf. on Robotics and Automation (ICRA'10), Anchorage, USA, May 2010.*

The present invention very cleverly uses hierarchized inverse kinematics for the exercise mode by taking as the task of highest priority (task 0) a task of fixedly keeping the feet of the exoskeleton 1. More precisely, said task of highest priority ensures control of the feet of the exoskeleton 1, advantageously in position and rotation (6D), and has instructions that these feet must not move. To the extent that it is the highest priority task, it is the strongest constraint, and it is thus guaranteed that the feet of the exoskeleton 1 remain on the ground, even if less priority tasks are not fully accomplished, that is to say the exoskeleton does not have exactly the expected posture. Thus, it is permitted not to block the entire exoskeleton 1 as in the prior art.

Naturally, the hierarchized inverse kinematics further comprises at least one other task of controlling the rest of the exoskeleton 1, of lower priority, advantageously two, or even three, preferentially selected from:

a task of controlling (in position) the center of mass (CoM) of the exoskeleton 1, in particular for stabilization;

a task of controlling (in rotation) the pelvis of the exoskeleton 1, to make the movement more anthropomorphic;

a task of controlling the posture of the exoskeleton 1, to allow the algorithm to converge more quickly towards a viable solution.

Preferably, the hierarchized inverse kinematics comprises these four tasks hierarchized in decreasing order of priority (that is to say from the highest priority to the least priority):

task 0—the task of keeping the feet fixed;
task 1—the task of controlling the CoM of the exoskeleton 1;
task 2—the task of controlling the pelvis of the exoskeleton 1;
task 3—task of controlling the posture of the exoskeleton 1.

The following combinations of tasks can be implemented: tasks 0 and 1, tasks 0 and 2, tasks 0 and 3, tasks 0, 1 and 2, tasks 0, 1 and 3, tasks 0, 2 and 3, and tasks 0, 1, 2 and 3.

It is understood that in order the exoskeleton 1 seeks above all to keep the feet on the ground, then to place the CoM as desired and in a stable manner, and finally, if the first two conditions are met, to best place the pelvis as desired then the overall posture as desired.

Examples of control loops for each of these tasks will be seen in detail later.

Method

Figure 2:
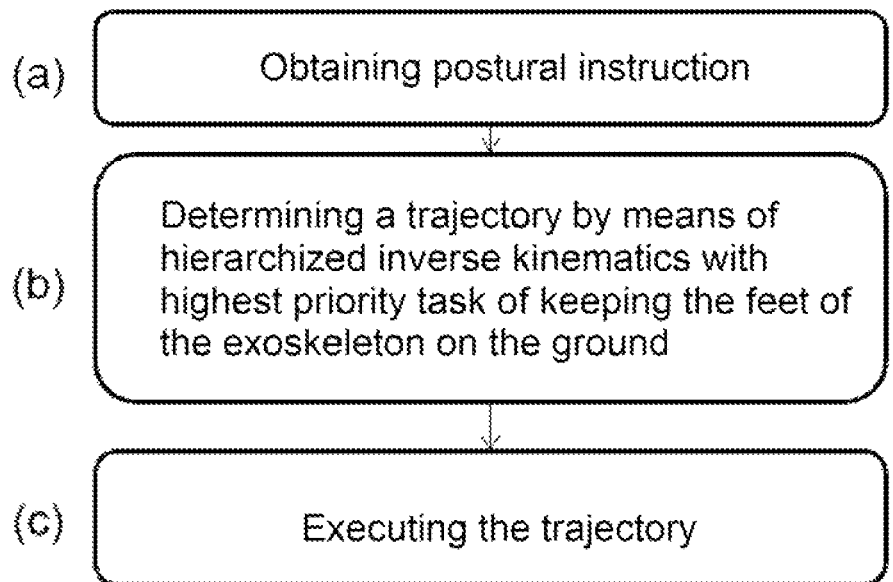
FIG. 2 is a diagram illustrating a preferred embodiment of the method according to the invention.

With reference to FIG. 2, said method for moving the exoskeleton 1, implemented by the on-board data processing means 11, begins with a step (a) of obtaining at least one postural instruction to be applied by the exoskeleton 1, in order for the operator to perform an exercise movement. Postural instruction means a CoM and/or joint instruction defining the desired pose of the exoskeleton. For example, for a squat there is an instruction to bend the knees. It is understood that each postural instruction may be of interest for all or part of the tasks. For example, the CoM instruction is of course of interest for the task of controlling the CoM but not that of keeping the feet on the ground.

In known manner, step (a) may comprise the identification of a movement intention by the operator, from data acquired by sensors; and determining the postural instruction from said movement intention, while respecting constraints.

To identify the intention of movement, the operator can be equipped, as explained, with a sensor vest 15 allowing to detect the configuration of his bust (orientation thereof) and/or a remote control.

The center of mass instruction can, in turn, be determined using the inertial measurement means 14.

The idea is advantageously to calculate for example the instruction from a pitch angle and/or a roll angle of the operator's torso determined from inertial measurements (noted pitch_angle and roll_angle), optionally after comparison with a predetermined threshold, in particular for the pitch angle. If we are below the threshold, the exoskeleton 1 is in "balance" mode: it assists the left/right and forward/backward movements of the operator while keeping the stability of the system.

A proportional law can be applied and the instruction $c'$ of CoM can be calculated in the following way: $c_x = K_r*$pitch_angle and: $c_y = K_r*$roll_angle.

Above this same threshold for the pitch angle, the exoskeleton is in "squat" mode: the greater the angle, the more the exoskeleton puts itself in a semi-squat posture: the proportional law for the roll can be kept (that is to say $c_y = K_r*$roll_angle) but advantageously a geometric law linking the pitch angle to a posture leading to a semi-squat is used for the pitch, and then a postural instruction relating to the joints of the exoskeleton 1 defining said semi-squat posture is obtained, rather than specific instructions on $c_x$.

In the same way, to make the movements more anthropomorphic and pleasant for the operator, the exoskeleton can assist the lateral flexion movements of the back and calculate an instruction $c'$ for a pelvis pose in particular also by a proportional law: $c_{roll\_angle\_pelvis}=K_r*roll\_angle$.

It will be understood that there is no limitation to a particular strategy for defining postural instructions, and that the number and nature of these instructions can be very different from one exercise movement to another. The person skilled in the art will know how to define the postural instructions of their choice, and the exoskeleton 1 will know how to use them in all cases.

Then, in step (b), as explained, a trajectory of the exoskeleton 1 is determined during which the feet remain on the ground by the implementation of said hierarchized inverse kinematics according to the determined postural instruction (s), with the task of highest priority which is the task of keeping the feet of the exoskeleton 1 on the ground as the operator performs the exercise movement.

Preferably, step (b) may further previously comprise the conversion of the center of mass instruction into a center of mass acceleration instruction via a "flexibility" stabilization and compensation algorithm.

More precisely, the exoskeleton 1 cannot be considered as a "rigid robot", that is to say an articulated system whose dynamics can be sufficiently well described by the conventional equations of rigid robotics:

The operator in the exoskeleton 1 is itself a source of potentially significant disturbances;

Parts of the exoskeleton are deformable (in particular ankle and/or hip), which results in particular in the fact that when the operator leans to the side, the CoM is generally further away and can potentially move out of its stability area.

The present method very cleverly resolves these difficulties by taking into account a flexibility model of the exoskeleton 1 in relation to a rigid robot for said instruction conversion.

As such, said task of controlling the CoM of the exoskeleton 1 is preferably a task of position control and stabilization of the CoM via a controller based on a flexible inverted pendulum model, see for example the document *Estimation and Stabilization of Humanoid Flexibility Deformation Using Only Inertial Measurement Units and Contact Information. Mehdi Benallegue, Florent Lamiraux. International Journal of Humanoid Robotics, World Scientific Publishing, 2015.*

Finally, in a step (c), said trajectory is executed to accomplish the exercise movement.

Task Control Loops

In known manner, the method comprises the execution of control loops defining for each task the evolution of the position of the exoskeleton 1 (that is to say the vector of joint positions) so as to implement said determined trajectory, that is to say so as to move the exoskeleton 1. It is understood that the execution of these loops allows the real-time implementation of steps (b) and (c).

Overall, there is one loop per task, and the hierarchized inverse kinematics is in practice implemented within said control loops.

Thus, for example, for task 0 there is a control loop on the position/orientation of the feet, for the task 1 a control loop on the position of the CoM, for the task 2 a control loop on the orientation of the pelvis and/or for the task 3 a control loop on the posture.

With reference to FIGS. 3a and 3b it is possible to have two types of control loops:

The first control loop, an example of which is illustrated in FIG. 3a, is for the task of keeping the feet of the exoskeleton 1 on the ground, as well as the possible tasks of controlling the pelvis of the exoskeleton and controlling the exoskeleton posture 1;

The second control loop, an example of which is illustrated in FIG. 3b, is specific to the task of controlling the CoM.

An embodiment of each of the loops will now be described in more detail, even if it will be understood that any control loop taking as input, for a given task, the postural instruction(s) of interest with respect to the task, and implementing inverse kinematics and at least one controller can be used.

In the example of FIG. 3a (first loop), the postural instructions of interest with regard to the task are noted $x_i^t$, $\dot{x}_i^t$, $\ddot{x}_i^t$, in particular the expected positions/orientations of a body or part of the exoskeleton 1 involved in the task, their derivatives (speeds) and second derivatives (accelerations). For example, for the task of keeping the feet of the exoskeleton 1 on the ground, it involves the position/orientation of the feet (6D) which must remain constant (that is to say zero derivatives and second derivatives).

Then the loop comprises the calculation of an error noted $e$, $\dot{e}$ between these instructions and the corresponding estimated values in the current state of the exoskeleton 1 $\hat{x}_i^t$, $\hat{\dot{x}}_i^t$ (that is to say the estimated positions/orientations of the body or the part of the exoskeleton 1 involved in the task, for example the estimated position of the feet of the exoskeleton 1).

A first controller, for example Proportional Derivative (PD), calculates a command $\ddot{x}^*_t$ from the errors and positions/speeds to be applied (called targets) of the degrees actuated $q^*$, $\dot{q}^*$.

The hierarchized inverse kinematics can then be implemented on the task stack (IK+SoT), preferably by applying the algorithm proposed in the document mentioned above *A Dedicated Quadradic Program for Fast Hierarchized-Inverse-Kinematic Resolution. A. Escande, N. Mansard and P-B. Wieber. In IEEE Int. Conf. on Robotics and Automation (ICRA'10), Anchorage, USA, May 2010,* to precisely determine the target accelerations of the actuated degrees $\ddot{q}^*$, and one or two integrations allow to find the target positions/speeds of the actuated degrees $q^*$, $\dot{q}^*$.

A Low Level Controller (LLC) allows to control the actuators of the exoskeleton based on the targets $q^*$, $\dot{q}^*$, $q^*$ and the instantaneous state $q$, $\dot{q}$ of the degrees of freedom of the exoskeleton 1.

Advantageously, a deformation estimator based on inertial measurements estimates "real" positions/speeds of the actuated degrees $\hat{q}$, $\hat{\dot{q}}$ (corresponding to a correction of the values $q$, $\dot{q}$ taking into account the flexibilities), using for example the algorithm described in the document Vigne, Matthieu, and al. *"State Estimation for a Legged Robot With Multiple Flexibilities Using IMU s: A Kinematic Approach." IEEE Robotics and Automation Letters* 5.1 (2019): 195-202.

Finally, direct kinematics allows to deduce the estimated values $\hat{x}_i^t$, $\hat{\dot{x}}_i^t$ corresponding to the instructions (that is to say the positions/orientations of the body or the part of the exoskeleton 1 involved in the task).

In the example of FIG. 3*b*, $c^t$, $\dot{c}^t$ denotes the postural instructions of interest with regard to the task of controlling the CoM, that is to say the CoM instruction. Note that there is no acceleration instruction yet since in the preferred mode it is derived via an algorithm for stabilization and compensation of the flexibilities of the exoskeleton 1, which is advantageously said controller based on a flexible inverted pendulum model, advantageously of linear-quadratic type (LQR, Linear—quadratic regulator). The output $\ddot{c}^*$ is a command in the same way as $\ddot{x}^*_i$ for other tasks.

In the same way as in the first loop, the hierarchized inverse kinematics can then be implemented on the task stack (IK+SoT), preferably by applying the algorithm proposed in the document mentioned above *A Dedicated Quadradic Program for Fast Hierarchized-Inverse-Kinematic Resolution. A. Escande, N. Mansard and P-B. Wieber. In IEEE Int. Conf. on Robotics and Automation (ICRA'10),* Anchorage, USA, May 2010, to precisely determine the target accelerations of the actuated degrees $\ddot{q}^*$, and one or two integrations allow to find the target positions/speeds of the actuated degrees $q^*, \dot{q}^*$.

The same Low Level Controller (LLC) allows to control the actuators of the exoskeleton based on the targets $q^*$, $\dot{q}^*$, $\ddot{q}^*$ and the instantaneous state $q$, $\dot{q}$ of the degrees of freedom of the exoskeleton 1.

Advantageously, a deformation estimator based on inertial measurements again estimates "real" positions/speeds of the actuated degrees $\hat{q}$, $\dot{\hat{q}}$ (corresponding to a correction of the values $q$, $\dot{q}$ by taking into account the flexibilities), using for example the algorithm described in the document Vigne, Matthieu, and al. *"State Estimation for a Legged Robot With Multiple Flexibilities Using IMU s: A Kinematic Approach."* IEEE Robotics and Automation Letters 5.1 (2019): 195-202.

Finally, direct kinematics allows to deduce the estimated values $\hat{c}^t$, $\dot{\hat{c}}^t$ corresponding to the instructions (that is to say the estimated position/speed of the CoM).

Equipment and System

According to a second aspect, the invention relates to the exoskeleton 1, for implementing the method according to the first aspect.

The exoskeleton 1 comprises data processing means 11 configured for implementing the method according to the first aspect, as well as if necessary data storage means 12, inertial measurement means 14 (inertia unit), means for detecting the impact of the feet on the ground 13 (contact sensors or possibly pressure sensors), and/or a vest equipped with sensors 15.

It has a plurality of degrees of freedom including at least one degree of freedom actuated by an actuator commanded by the data processing means 11.

Computer Program Product

According to a third and a fourth aspect, the invention relates to a computer program product comprising code instructions for the execution (on the processing means 11), of a method according to the first aspect of moving an exoskeleton 1, as well as storage means readable by computer equipment on which this computer program product is located.

The invention claimed is:

1. A method for moving a bipedal exoskeleton accommodating a human operator, including the implementation, by data processing means of the exoskeleton, of steps of:

(a) obtaining at least one postural instruction to be applied by the exoskeleton in order for the operator to perform an exercise movement;

(b) determining a trajectory of the exoskeleton by means of hierarchized inverse kinematics based on the at least one postural instruction, said hierarchized inverse kinematics comprising a stack of hierarchized tasks comprising, as a task of highest priority, a task of keeping feet of the exoskeleton on the ground as the operator performs said exercise movement;

wherein the stack of hierarchized tasks comprises, in decreasing order of priority, said task of keeping the feet of the exoskeleton on the ground, a task of controlling a center of mass, CoM, of the exoskeleton, a task of controlling a pelvis of the exoskeleton, and a task of controlling a posture of the exoskeleton.

2. The method according to claim 1, wherein step (a) comprises identifying a movement intention by the operator, from data acquired by sensors of the exoskeleton; and determining the at least one postural instruction from said movement intention.

3. The method according to claim 1, wherein the at least one postural instruction is a center of mass, CoM, and/or joint instruction defining a desired pose of the exoskeleton as the operator performs said exercise movement.

4. An exoskeleton comprising data processing means configured to implement the method according to claim 1 for moving the exoskeleton.

5. A non-transitory storage means readable by a computer equipment on which a computer program product comprises code instructions for executing the method according to claim 1 for moving an exoskeleton.

6. The method according to claim 1, wherein the task of controlling the CoM of the exoskeleton is a task of CoM position control and stabilization via a controller based on a flexible inverted pendulum model.

7. A method for moving a bipedal exoskeleton accommodating a human operator, including the implementation, by data processing means of the exoskeleton, of steps of:

(a) obtaining at least one postural instruction to be applied by the exoskeleton in order for the operator to perform an exercise movement;

(b) determining a trajectory of the exoskeleton by means of hierarchized inverse kinematics based on the at least one postural instruction, said hierarchized inverse kinematics comprising a stack of hierarchized tasks comprising, as a task of highest priority, a task of keeping feet of the exoskeleton on the ground as the operator performs said exercise movement:

wherein the stack of hierarchized tasks further comprises a task of controlling a center of mass, CoM, of the exoskeleton, of lower priority than said task of keeping the feet of the exoskeleton on the ground, wherein the task of controlling the CoM of the exoskeleton is a task of CoM position control and stabilization via a controller based on a flexible inverted pendulum model.

8. The method according to claim 7, wherein the stack of hierarchized tasks further comprises at least one further task of controlling the rest of the exoskeleton, different from the task of controlling the CoM of the exoskeleton, of lower priority than said task of keeping the feet of the exoskeleton on the ground.

9. The method according to claim 8, wherein said at least one further task of controlling the rest of the exoskeleton is selected from a task of controlling a pelvis of the exoskeleton;

a task of controlling a posture of the exoskeleton.

10. The method according to claim 8, wherein said at least one further task of controlling the rest of the exoskeleton is of lower priority than said task of controlling the CoM of the exoskeleton.

11. The method according to claim 8, wherein step (b) comprises executing control loops defining for each task of the stack of hierarchized tasks an evolution of a position of the exoskeleton so as to implement said trajectory.

12. The method according to claim 11, wherein there is an independent control loop per task, the hierarchized inverse kinematics being implemented within said control loops.

13. The method according to claim 11, wherein the exoskeleton has a plurality of degrees of freedom, including actuated degrees of freedom, and the position of the exoskeleton is defined by a vector of joint positions of the actuated degrees of freedom.

14. A method for moving a bipedal exoskeleton accommodating a human operator, including the implementation, by data processing means of the exoskeleton, of steps of:

(a) obtaining at least one postural instruction to be applied by the exoskeleton in order for the operator to perform an exercise movement;

(b) determining a trajectory of the exoskeleton by means of hierarchized inverse kinematics based on the at least one postural instruction, said hierarchized inverse kinematics comprising a stack of hierarchized tasks comprising, as a task of highest priority, a task of keeping feet of the exoskeleton on the ground as the operator performs said exercise movement;

wherein step (b) comprises executing control loops defining for each task of the stack of hierarchized tasks an evolution of a position of the exoskeleton so as to implement said trajectory.

12

15. The method according to claim 14, wherein there is an independent control loop per task, the hierarchized inverse kinematics being implemented within said control loops.

16. The method according to claim 14, wherein the exoskeleton has a plurality of degrees of freedom, including actuated degrees of freedom, and the position of the exoskeleton is defined by a vector of joint positions of the actuated degrees of freedom.

17. The method according to claim 14, wherein the stack of hierarchized tasks further comprises at least one task of controlling the rest of the exoskeleton, of lower priority than said task of keeping the feet of the exoskeleton on the ground.

18. The method according to claim 17, wherein said at least one task of controlling the rest of the exoskeleton is selected from a task of controlling a center of mass, CoM, of the exoskeleton;

a task of controlling a pelvis of the exoskeleton;

a task of controlling a posture of the exoskeleton.

19. The method according to claim 18, wherein the stack of hierarchized tasks comprises, in decreasing order of priority, said task of keeping the feet of the exoskeleton on the ground, the task of controlling the CoM of the exoskeleton, the task of controlling the pelvis of the exoskeleton, and the task of controlling the posture of the exoskeleton.

20. The method according to claim 18, wherein the task of controlling the CoM of the exoskeleton is a task of CoM position control and stabilization via a controller based on a flexible inverted pendulum model.

* * * * *